United States Patent
Fan et al.

(10) Patent No.: US 12,195,791 B2
(45) Date of Patent: Jan. 14, 2025

(54) TARGET ENRICHMENT VIA ENZYMATIC DIGESTION IN NEXT GENERATION SEQUENCING

(71) Applicant: Saint Louis University, St. Louis, MO (US)

(72) Inventors: Xiaofeng Fan, St. Louis, MO (US); Adrian Michael Di Bisceglie, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 905 days.

(21) Appl. No.: 17/173,858

(22) Filed: Feb. 11, 2021

(65) Prior Publication Data

US 2021/0246496 A1    Aug. 12, 2021

Related U.S. Application Data

(60) Provisional application No. 62/972,914, filed on Feb. 11, 2020.

(51) Int. Cl.
*C12Q 1/68* (2018.01)
*C12Q 1/6806* (2018.01)
*C12Q 1/6848* (2018.01)

(52) U.S. Cl.
CPC ......... *C12Q 1/6848* (2013.01); *C12Q 1/6806* (2013.01); *C12Q 2521/319* (2013.01); *C12Q 2525/125* (2013.01); *C12Q 2531/107* (2013.01); *C12Q 2531/125* (2013.01)

(58) Field of Classification Search
CPC ... C12Q 1/6848; C12Q 1/6806; C12Q 1/6869
See application file for complete search history.

(56) References Cited

U.S. PATENT DOCUMENTS

| | | | |
|---|---|---|---|
| 7,786,294 B2 | 8/2010 | Fan et al. | |
| 2017/0037459 A1 | 2/2017 | Godwin | |
| 2021/0147919 A1* | 5/2021 | Sapolsky | C12Q 1/6837 |
| 2021/0147920 A1* | 5/2021 | Shapero | C12Q 1/6827 |
| 2021/0246496 A1* | 8/2021 | Fan | C12Q 1/6869 |
| 2022/0333186 A1* | 10/2022 | Brown | C12Q 1/6806 |

FOREIGN PATENT DOCUMENTS

WO    WO2012003374    *  3/2014

OTHER PUBLICATIONS

Grime SK, Martin RL, Holaway BL. Inhibition of restriction enzyme cleavage of DNA modified with 7-deaza-dGTP. Nucleic Acids Res. May 25, 1991;19(10):2791. doi: 10.1093/nar/19.10.2791. PMID: 1645867; PMCID: PMC328214. (Year: 1991).*
Van Emmerik CL, Gachulincova I, Lobbia VR, Daniëls MA, Heus HA, Soufi A, Nelissen FHT, van Ingen H. Ramified rolling circle amplification for synthesis of nucleosomal DNA sequences. Anal Biochem. Jan. 1, 2020;588:113469. doi: 10.1016/j.ab.2019.113469. Epub Oct. 9, 2019. PMID: 31604067. (Year: 2019).*
Takahashi, H., Ohkawachi, M., Horio, K. et al. RNase H-assisted RNA-primed rolling circle amplification for targeted RNA sequence detection. Sci Rep 8, 7770 (2018) (Year: 2018).*
Rockett R, Barraclough KA, Isbel NM, Dudley KJ,. Specific rolling circle amplification of low-copy human polyomaviruses BKV, HPyV6, HPyV7, TSPyV, and STLPyV. J Virol Methods. Apr. 2015;215-216:17-21. doi: 10.1016/j.jviromet.2015.02.004. Epub Feb. 16, 2015. PMID: 256984 (Year: 2015).*
Stevens H, Rector A, Van Ranst M. Multiply primed rolling-circle amplification method for the amplification of circular DNA viruses. Cold Spring Harb Protoc. 2010 (Year: 2010).*
Lee ST, Kim JY, Kown MJ, Kim SW, Chung JH, Ahn MJ, Oh YL, Kim JW, Ki CS. Mutant enrichment with 3'-modified oligonucleotides a practical PCR method for detecting trace mutant DNAs. J Mol Diagn. 2011 (Year: 2011).*
J, Li XY, Du YC, Zhang LN, Liu KK, Zhu LN, Kong DM. Sensitive fluorescent detection of DNA methyltransferase using nicking endonuclease-mediated multiple primers-like rolling circle amplification. Biosens Bioelectron. May 15, 2017;91:417-423. doi: 10.1016/j.bios.2016.12.061. Epub Dec. 30, 2016. (Year: 2017).*
Ducani C, Bernardinelli G, Högberg B. Rolling circle replication requires single-stranded DNA binding protein to avoid termination and production of double-stranded DNA. Nucleic Acids Res. 2014;42(16):10596-604. doi: 10.1093/nar/gku737. Epub Aug. 12, 2014. PMID: 25120268; PMCID: PMC4176320. (Year: 2014).*
Nilsson M, Antson DO, Barbany G, Landegren U. RNA-templated DNA ligation for transcript analysis. Nucleic Acids Res. Jan. 15, 2001;29(2):578-81. doi: 10.1093/nar/29.2.578. PMID: 11139629; PMCID: PMC29667. (Year: 2001).*
Dean, et al., "Rapid Amplification of Plasmid and Phage DNA Using Phi29 DNA Polymerase and Multiply-Primed Rolling Circle Amplification", *Genome Research*, 11(6):1095-9, 2001.
Fan et al., "Efficient amplification and lconing of near full-length hepatitis C Virus genome from clinical samples", *Biochem Biophy Res Communi*, 346(4):1163-72, 2006.
Gansauge et al., "Single-stranded DNA library preparation from highly degraded DNA using T4 DNA ligase", *Nucleic Acids Research*, 45(10):1-10, 2017.
Gorse et al., "Interpatient mutational spectrum of human coronavirus-OC43 revealed by illumine sequencing", *J. Med. Virol.*, 89:1330-1338, 2017.
Guria et al., "Circular RNA Profiling by Illumina Sequencing via Template-Dependent Multiple Displacement Amplification", *BioMed Research International*, 2019:2756516, 2019.
Li et al., "Full annotation of serum virome in Chinese blood donors with elevated alanine aminotransferase levels", *Transfusion*, 59, 3177-3185; 2019.
Peng et al., "A novel target enrichment strategy in next-generation sequencing through 7-deaza-dGTP-resistant enzymatic digestion", *BMC Research Notes*, 13:445, 2020.

(Continued)

*Primary Examiner* — Gary Benzion
*Assistant Examiner* — Olayinka A Oyeyemi
(74) *Attorney, Agent, or Firm* — Parker Highlander PLLC (57) ABSTRACT

Provided herein are methods of preparing a template nucleic acid for next-generation sequencing. The methods comprise performing primer extension using $c^7$dGTP instead of dGTP, which then allows for the input nucleic acids to be selectively digested by $c^7$dGTP-resistant restriction enzymes, thereby enriching the template nucleic acid prior to next-generation sequencing library preparation.

18 Claims, 3 Drawing Sheets

Specification includes a Sequence Listing.

(56) References Cited

OTHER PUBLICATIONS

Ren et al., "Evidence for deleterious hepatitis C virus quasispecies mutation loads that differentiate the response patters in IFN-based antiviral therapy", *Journal of General Virology*, 97, 334-343, 2016.

Ren et al., "In-depth serum virome analysis in patients with acute liver failure with indeterminate etiology", *Arch Virol*, 165(1): 127-135, 2020.

Wang et al., "Template-dependent multiple displacement amplification for profiling human circulating RNA", *BioTechniques* 63:21-27, 2017.

\* cited by examiner

SEQUENCE LISTING

```
<160> NUMBER OF SEQ ID NOS: 14

<210> SEQ ID NO 1
<211> LENGTH: 14
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(6)
<223> OTHER INFORMATION: n is a, t, g, or c

<400> SEQUENCE: 1
nnnnnngcga tcgc                                                       14

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
actctctcgt ccccttctcc                                                 20

<210> SEQ ID NO 3
<211> LENGTH: 21
```

```
<212> TYPE: DNA
<213> ORGANISM: Artificial sequence
<220> FEATURE:
<223> OTHER INFORMATION: Synthetic oligonucleotide

<400> SEQUENCE: 3
tgacggaagg aaagaagtca g                                             21

<210> SEQ ID NO 4
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 4
ccttctccgt ctgccgttc                                                19

<210> SEQ ID NO 5
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 5
ggaaggaaag aagtcagaag gc                                            22

<210> SEQ ID NO 6
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 6 gcgatcgc                                                             8

<210> SEQ ID NO 7
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 7
aacaggcttt cactttctcg c                                             21

<210> SEQ ID NO 8
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 8
cgagggagtt cttcttctag gg                                            22

<210> SEQ ID NO 9
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 9
```

-continued

```
gcgatcgctc cacactccga aagagacc                                              28
```

<210> SEQ ID NO 10
<211> LENGTH: 6
<212> TYPE: DNA
<213> ORGANISM: Artificial sequence
<220> FEATURE:
<223> OTHER INFORMATION: Synthetic oligonucleotide

<400> SEQUENCE: 10

```
cgatcg                                                                       6
```

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11

```
tccacactcc gaaagagacc                                                       20
```

<210> SEQ ID NO 12
<211> LENGTH: 14
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(6)
<223> OTHER INFORMATION: n is a, t, g, or c

<400> SEQUENCE: 12

```
nnnnnnaggt gtgt                                                             14
```

<210> SEQ ID NO 13
<211> LENGTH: 8
<212> TYPE: DNA
<213> ORGANISM: Artificial sequence
<220> FEATURE:
<223> OTHER INFORMATION: Synthetic oligonucleotide

<400> SEQUENCE: 13

```
tgtgtgga                                                                     8
```

<210> SEQ ID NO 14
<211> LENGTH: 5
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(5)
<223> OTHER INFORMATION: n is a, t, g, or c

<400> SEQUENCE: 14

```
nnnnn                                                                        5
```

TARGET ENRICHMENT VIA ENZYMATIC DIGESTION IN NEXT GENERATION SEQUENCING

REFERENCE TO RELATED APPLICATIONS

The present application claims the priority benefit of U.S. provisional application No. 62/972,914, filed Feb. 11, 2020, the entire contents of which is incorporated herein by reference.

STATEMENT REGARDING FEDERALLY SPONSORED RESEARCH

This invention was made with government support under Grant No. AI139835 awarded by the National Institutes of Health. The government has certain rights in the invention.

REFERENCE TO A SEQUENCE LISTING

The instant application contains a Sequence Listing, which has been submitted in ASCII format via EFS-Web and is hereby incorporated by reference in its entirety. Said ASCII copy, created on Feb. 11, 2021, is named USTLP0122US_ST25.txt and is 3.3 kilobytes in size.

BACKGROUND

1. Field

The present invention relates generally to the field of molecular biology. More particularly, it concerns methods of preparing a template nucleic acid for next-generation sequencing.

2. Description of Related Art

Next-generation sequencing (NGS) has become a common method in biomedical research and clinical medicine. When sequencing an explicit target, e.g., HIV (note that it could be any virus, bacteria, or genome of biological interest), from a patient blood sample, NGS suffers from a significant shortcoming. By quantity, HIV-derived nucleic acids in a blood sample makes up a very small portion, with most of the genetic material in the sample being of human origin. Consequently, in the NGS output, HIV sequences account for a very low percentage, usually less than 1%, and more than 99% of the output sequences are human sequences and/or are background. To solve this issue, industry provides an option in which HIV-specific sequences from a blood sample are baited using HIV baits, a procedure called target enrichment or capture sequencing. This procedure is costly, tedious, and sometimes insufficient owing to off-target effects. Alternative options that achieve equal or higher efficiency with a much cheaper and simpler procedure are needed.

SUMMARY

In one embodiment, provided herein are methods of preparing a nucleic acid template for next-generation sequencing, the method comprising: (a) incubating a population of nucleic acid molecules comprising the template nucleic acid with a primer, $c^7dGTP$, dCTP, dATP, dTTP, and a DNA polymerase; (b) incubating the product of step (a) with a splinter oligonucleotide and T4 DNA ligase under conditions to allow for the self-ligation of the extension product of step (a); and (c) incubating the product of step (b) with $c^7dGTP$-resistant restriction enzymes, Exonuclease I, and Exonuclease III under conditions to allow for the digestion of non-target and background nucleic acid, including, for example, the template nucleic acid.

In some aspects, the template nucleic acid is DNA. In some aspects, the DNA polymerase used in step (a) is a DNA-dependent DNA polymerase.

In some aspects, the template nucleic acid is RNA. In some aspects, the DNA polymerase used in step (a) is an RNA-dependent DNA polymerase.

In some aspects, the $c^7dGTP$-resistant restriction enzymes are one or more of AluI, HaeIII, and HpyCH4V. In some aspects, the $c^7dGTP$-resistant restriction enzymes are enzymes that are unable to cleave nucleic acid molecules that have one or more $c^7dGTP$ within the enzyme's target sequence.

In some aspects, the primer comprises a phosphate on the 5' end. In some aspects, the 3' end of the primer has a sequence that hybridizes to the template nucleic acid. In some aspects, the 3' end of the primer has a degenerate sequence. In some aspects, the 3' end of the primer has a poly-T sequence.

In some aspects, step (a) comprises 5-10 cycles of primer extension. In some aspects, the splinter oligonucleotide hybridizes to the rare restriction site at the 5' end of the primer used in step (a). In some aspects, the splinter oligonucleotide has a C3 spacer at its 3' end. In some aspects, the splinter oligonucleotide has a degenerate sequence at its 5' end.

In some aspects, the product of step (a) is purified prior to performing step (b). In some aspects, the methods further comprise (d) incubating the product of step (c) with a primer that hybridizes to the primer used in step (a), dNTPs, and a DNA polymerase under conditions to allow for rolling circle amplification. In some aspects, the DNA polymerase is phi29 DNA polymerase. In some aspects, the 6-nt primer comprises phosphorothioate bonds.

In some aspects, the methods further comprise (e) incubating the product of step (d) with degenerate primers (e.g., SEQ ID NO: 14), dNTPs, and a DNA polymerase under conditions to allow for multiple displacement amplification. In some aspects, the reaction of step (e) is heat inactivated. In some aspects, the reaction of step (c) is heat inactivated prior to performing step (d). In some aspects, steps (b) through (e) are performed in the same tube. In some aspects, steps (b) through (e) are performed without exchanging the buffer. In some aspects, steps (b) through (e) are performed without removing any components from the previous reactions. In some aspects, steps (b) through (e) are performed without any intervening purification steps.

In some aspects, the template nucleic acid is a rare species within the population of nucleic acid molecules. In some aspects, the template nucleic acid is a viral or bacterial species and the population of nucleic acid molecules comprises nucleic acid molecules extracted from a patient sample. In some aspects, the template nucleic acid is a poorly expressed RNA and the population of nucleic acid molecules comprises nucleic acid molecules extracted from a patient sample. In some aspects, the template nucleic acid is a fusion gene and the population of nucleic acid molecules comprises nucleic acid molecules extracted from a patient sample.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, the variation that exists among the study subjects, or a value that is within 10% of a stated value.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 5A-5C. HBV-specific read mapping among four options. HBV-mapped reads were normalized as the number per million reads (FIG. 5A); Read-alignment viewed in bam file (FIG. 5B). Option 4 had no HBV fragment spiked in the serum and served as a control.

DETAILED DESCRIPTION

Figure 1:
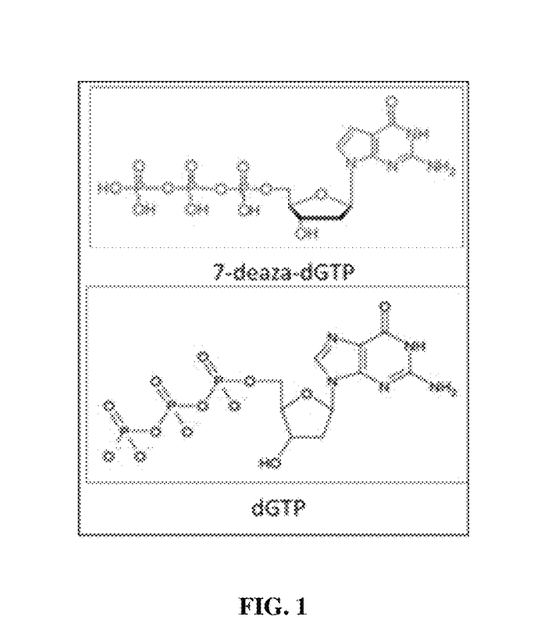
FIG. 1. Molecular structure of dGTP and $c^7$dGTP.

Next-generation sequencing (NGS) has two major limiting factors: low sensitivity and easy contamination. NGS consists of three steps: template preparation, library construction, and sequencing (Head et al., 2014). The present invention targets the step of template preparation. The Target Enrichment via Enzymatic Digestion in Next-Generation Sequencing (TEEDseq) methods provided herein solve both the sensitivity and contamination issues by utilizing 7-deaza-2'-deoxyguanosine 5'-triphosphate ($c^7$dGTP) in a primer extension reaction instead of regular deoxyguanosine triphosphate (dGTP). $c^7$dGTP is an analog of deoxyguanosine triphosphate (dGTP) (FIG. 1). Owing to its ability to relax DNA secondary structure, it has been widely used in polymerase chain reaction (PCR) for authentic amplification of GC-rich templates, Sanger sequencing, and primer extension to determine transcription initiation sites (McConlogue et al., 1988; Motz et al., 2000; Broadbent et al., 2010). DNA molecules containing $c^7$dGTP shows steric alteration that results in the resistance to some restriction enzymes when their recognition motifs contain guanosine (Grime et al., 1991). For example, the AluI, HaeIII, and HpyCH4V restriction enzymes will digest the primer extension template and non-extended sequences, but not the primer extension product, thereby achieving an effective target enrichment. As such, provided herein are methods of enriching biological DNA molecules in preparation for next-generation sequencing (NGS) by using $c^7$dGTP.

Figure 2:
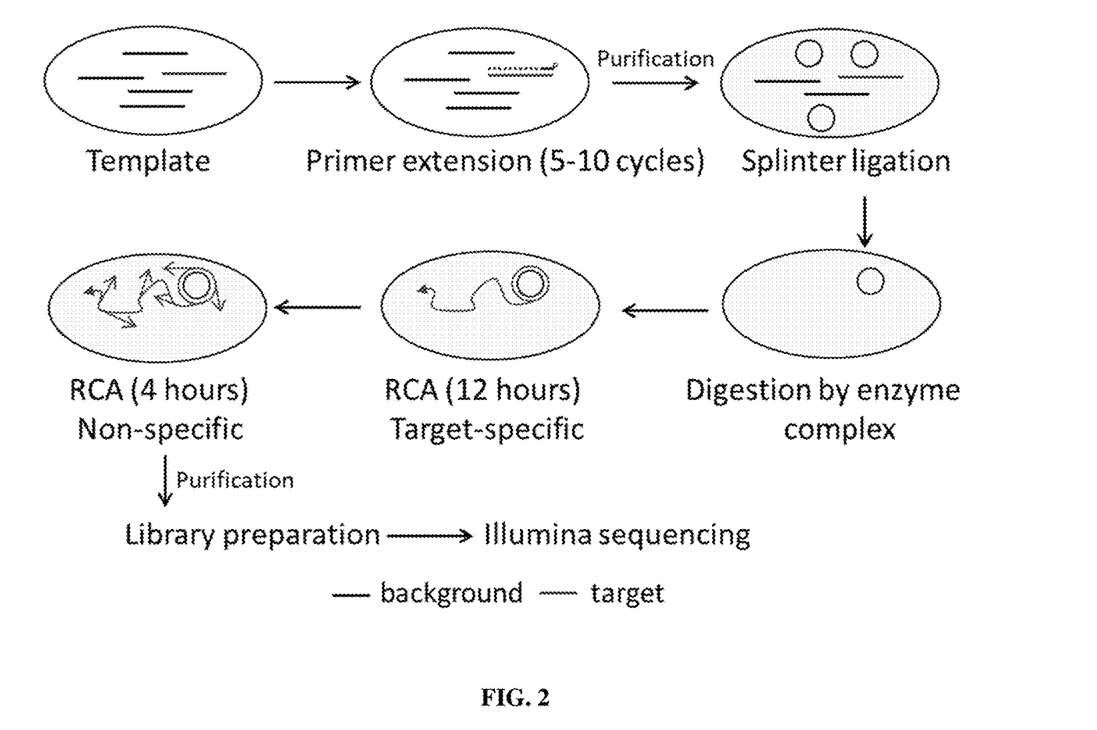
FIG. 2. A working flow of TEEDseq. Note that ligation, digestion, and RCA (grey-filled circles) are performed in the same tube in a sequential manner. RCA, rolling cycling amplification.

The TEEDseq workflow has four primary steps (FIG. 2). As shown in FIG. 2, splinter ligation, digestion by enzyme complex, and two-step RCA are performed sequentially in the same tube, thereby reducing the chance of contamination.

The input template into the TEEDseq workflow can be DNA or RNA extracted from any source for which analysis is desired. For example, the input template can be DNA or RNA extracted from a patient sample. Depending on the nature of primers used in the primer extension step, TEEDseq could be used for target-specific (gene/transcript-specific primers) or whole transcriptome/genome profiling (random primers). In the case of an RNA template, reverse transcription is applied instead of DNA polymerase-based primer extension.

Figure 3:
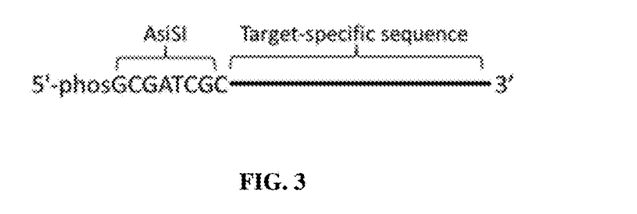
FIG. 3. Primer design in certain embodiments of TEEDseq. The AsiSI target sequence is provided by SEQ ID NO: 6.

The input template is first subjected to a primer extension reaction having about 5-10 cycles. Target DNA molecule is captured by a low number of cycles of target-specific primer extension in which dGTP is completely replaced by $c^7$dGTP. When the template is heterogeneous, high number of cycles should be avoided to prevent the formation of a PCR product resulting from non-specific priming. Depending on the nature of the target, single or multiple primers can be used in this step. The 5' end of each primer is a phosphate to facilitate the self-circulation in the next step (FIG. 3). The 3' end of each primer may be target-specific to eliminate template-independent (background) amplification and allow only for target gene or target transcript amplification. Alternatively, the 3' end of each primer may be random to allow for whole transcriptome profiling or whole genome profiling. Alternatively, the 3' end of each primer may be a poly-T sequence to allow for whole transcriptome profiling.

In certain aspects, the 5' end the primer also contains an 8-nt AsiSI restriction site (5'-GCG ATC GC-3'; SEQ ID NO:

6) that serves as a universal site for splinter ligation, a universal priming site for rolling circle amplification (RCA), a means to decipher the spectrum of template sizes when the final MDA product is digested by AsiSI, and a unique molecular identifier (UMI) in bioinformatic analysis to infer relative amounts of small-size DNA molecules in NGS data. The selection of AsiSI was based on its rarity in the human genome. Using HiCUP (Wingett et al., 2015), AsiSI has only 1,231 cuts on build GRCh38. AsiSI is also rare among microbial and viral genomes. For example, there are no AsiSI recognition motifs among 1,809 full-length hepatitis C virus (HCV) genomes from the Los Alamos HCV database and 2,899 full-length hepatitis B virus (HBV) genomes from the HBV database (Kuiken et al., 2005; Hayer et al., 2013).

Next, the primer extension product is subjected to a splinter ligation reaction. A splinter, is applied to facilitate self-ligation. Its 3' end is blocked by C3 spacer. Under the mechanism revealed by Kwok et al. (2013), splinter-mediated ligation, by T4 DNA ligase, is highly efficient (Gansauge et al., 2017; McDonald et al., 2019). In certain aspects, the splinter may have a sequence of 5'-NNNNNNGC-GATCGCSp3-3' (SEQ ID NO: 1).

Following splinter ligation, the circularized product is subjected to digestion by an enzyme complex that includes five enzymes: two exonucleases (Exonuclease I and Exonuclease III) and three restriction enzymes (AluI, HaeIII, and HpyCH4V). Exonuclease I and Exonuclease III are used to digest linear single-strand (ss) and double-strand (ds) DNA (Dahl et al., 2004). AluI, HaeIII, and HpyCH4V were carefully selected based on the following reasons. First, their recognition motifs are 4-bp and together have 36,535,384 cuts (AluI 13,085,321; HaeIII 8,582,925; HpyCH4V 14,867, 138) on the human genome (build GRCh38). Second, both ss and ds DNA with dGTP replaced by $c^7dGTP$ are resistant to these enzymes. Finally, they have the same reaction condition as Exonuclease I and Exonuclease III. Therefore, these five enzymes can be used together as a complex that digests non-circular and background circular ssDNA and dsDNA.

The digested product is then subjected to two-step rolling circle amplification (RCA), first using a 6-nt primer that hybridizes to the primer extension primer, and then by random hexamer primers. The use of a 6-nt primer, rather than 7- or 8-nt, was chosen because RCA uses phi29 DNA polymerase, which is functionally optimized at 30° C.

In certain aspects, the 6-nt primer may hybridize to the AsiSI site in the primer extension primer. AsiSI contains three 6-nt strings, GCGATC, CGATCG, and GATCGC, which respectively has 141,017, 14,185, and 143,339 cuts on the human genome. Therefore, CGATCG is ideally used as the universal primer for RCA to generate tandem copies of each circular DNA molecule.

New England Biolabs has developed a CutSmart buffer that is compatible among enzymes, including the five enzymes used for digestion and phi29 DNA polymerase used for RCA. Therefore, the steps of digestion and RCA are conducted sequentially in the same tube without the need for purification at each step (FIG. 2).

In comparison to other target-enrichment methods, such as hybridization-based probe baiting (Illumina: Target enrichment), TEEDseq is much simpler and cheaper. It is estimated that the cost of TEEDseq per sample is about 10% that of probe-based methods.

Hybridization-based methods have an enrichment step after NGS library preparation (Illumina: Target enrichment). In contrast, TEEDseq has the enrichment occurring during sample preparation prior to NGS library preparation. Therefore, TEEDseq is highly scalable from a single to hundreds of samples. In addition, PCR amplification after enrichment using TEEDseq is unnecessary.

TEEDseq is capable of preparing templates for both short-read sequencing (Illumina) and long-read sequencing (PacBio or Nanopore) because primer extension can generate templates up to 20,000 base pairs long. On the other hand, probe-based method can only be used for short-read sequencing like Illumina.

TEEDseq can be used to efficiently detect fusion genes.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

As a proof of concept showing the feasibility of TEEDseq, a recombinant plasmid containing a full-length hepatitis B virus (HBV) genome (3,321 bp) was used as the input template.

Figures 4A, 4B, 4C, 4D:
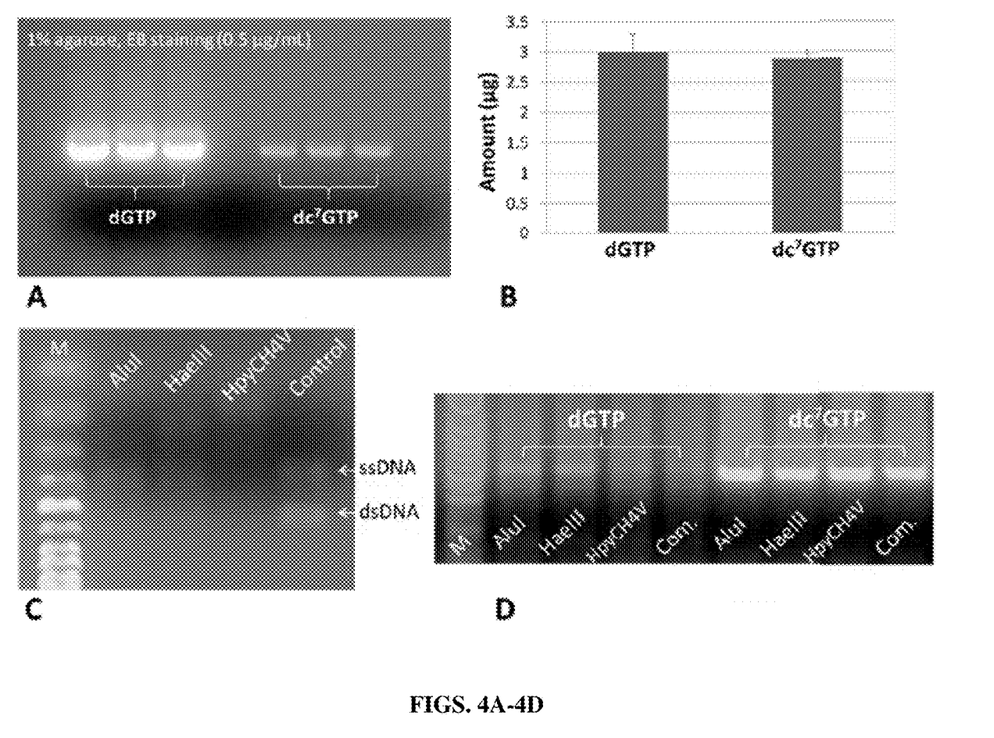
FIGS. 4A-4D. Characteristics of $c^7$dGTP-involved PCR amplification and digestion. PCR product with $c^7$dGTP was hard to stain with EB (FIG. 4A), but it had a similar yield to dGTP (FIG. 4B). All three enzymes gave complete digestion of dsDNA generated from PCR using dGTP (FIG. 4C) but not $c^7$dGTP, as examined via 35-cycle of PCR after digestion (FIG. 4D).

To test the efficiency of amplification reactions using $c^7dGTP$, the HBV plasmid was amplified using a 30-cycle PCR reaction in 50 µL containing 1×Q5 DNA polymerase buffer, 0.8 mM dNTPs, 0.4 µM of each forward and reverse primer (HBVF1, 5'-ACT CTC TCG TCC CCT TCT CC-3' (SEQ ID NO: 2); HBVR1, 5'-TGA CGG AAG GAA AGA AGT CAG-3' (SEQ ID NO: 3)), and 1 unit of Q5 DNA polymerase (NEB). In another reaction, dGTP was completely replaced by $c^7dGTP$ (Roche). A weak band on an ethidium bromide (EB)-stained gel was seen from the reaction using $c^7dGTP$ (FIG. 4A), which was consistent with previous reports that $c^7dGTP$ containing DNA does not stain well with EB (Weiss et al., 1994). As such, quantification using a NanoDrop was performed instead, which showed a slightly lower yield in PCR with $c^7dGTP$ (FIG. 4B). This slight drop in PCR yield may be attributed to the nature of $c^7dGTP$ rather than an authentic decrease. In summary, PCR with $c^7dGTP$ showed similar efficiency to that using regular dGTP.

To determine the resistance of $c^7dGTP$ to restriction enzymes, the PCR was repeated using a reverse primer containing a phosphate at its 5' end (HBVR1p; all primers described here were ordered from Integrated DNA Technologies). The resulting PCR product was purified and digested by Lambda exonuclease (NEB), which favors the digestion of 5' phosphate strands (Civit et al., 2012). Consequently, both ssDNA and dsDNA were generated and used for digestion by three restriction enzymes (AluI, HaeIII, and HpyCH4V) (NEB) that were carefully selected based on their recognition motifs and buffer compatibility. The PCR amplicon, 504 bp in length, had three AluI sites, one HaeIII site, and four HpyCH4V sites. While the three enzymes completely digested dsDNA, only HpyCH4V cut both ssDNA and dsDNA (FIG. 4C). The same experiment was performed using a PCR amplicon generated using $c^7dGTP$.

Since c⁷dGTP is difficult to stain (many dyes we tested were failed to stain), a 35-cycle PCR was conducted using an aliquot of 2 μL enzyme reaction with primers (HBVF2, 5'-CCT TCT CCG TCT GCC GTT C-3' (SEQ ID NO: 4) and HBVR2, 5'-GGA AGG AAA GAA GTC AGA AGG C-3' (SEQ ID NO: 5)). In comparison to dGTP, c⁷dGTP showed strong bands, suggesting resistance to digestion. Also, the combination of all three enzymes gave almost complete digestion of both ssDNA and dsDNA containing dGTP, as indicated by a weaker band, but not DNA containing c⁷dGTP (FIG. 4D). These experiments demonstrated that c⁷dGTP is resistant to individual or combinatorial digestion of AluI, HaeIII, and HpyCH4V.

Example 2

To test one workflow of TEEDseq, a 1,311-bp HBV fragment was generated from the plasmid (described above) by PCR with primers (forward, 5'-AAC AGG CTT TCA CTT TCT CGC-3' (SEQ ID NO: 7); reverse, 5'-CGA GGG AGT TCT TCT TCT AGG G-3' (SEQ ID NO: 8)). The PCR amplicon was gel-purified, quantified, and spiked in a serum sample from a healthy blood donor at a concentration of $1 \times 10^6$ copies/mL, which mimics the serum concentration of viruses like HCV and HBV. Total DNA was extracted from 0.5 mL of serum using a QIAamp MinElute ccfDNA Kit (Qiagen) and eluted into 20 μL Tris buffer. Th entire 20 μL of extracted DNA was used for a 5-cycle primer extension reaction using Q5 DNA polymerase and a reverse primer (5'-ᶠGCGATCGC TCC ACA CTC CGA AAG AGA CC-3' (SEQ ID NO: 9)). The reaction was purified using a MinElute PCR Purification Kit (Qiagen) and eluted into 20 μL Tris buffer, followed by ligation in a 30 μL reaction containing 10 U T4 DNA ligase and 0.5 μM of a splinter (5'-NNNNNNGCGATCGCSp3-3' (SEQ ID NO: 1); 3' end is blocked by a C3 spacer) at 14° C. overnight. After heat inactivation, enzyme complex (AluI 10 U, HeaIII 10 U, HpyCH4V 5 U, Exonuclease I 50 U, and Exonuclease III 20 U) was added to bring the volume up to 45 μL while maintaining 1× CutSmart buffer. Three hours after incubation at 37° C., the reaction was heat-inactivated and used for RCA with 1 μM AsiSI-specific primer (5'-CGAT*C*G-3' (SEQ ID NO: 10); asterisks denote phosphorothioate bonds to resist exonuclease activity of phi29 DNA polymerase) at 30° C. for 12 hours, followed by a 3-hour multiple displacement amplification (MDA) in which random hexamer primers were added into the tube at a final concentration at 50 μM. Multiple displacement amplification (MDA) is performed using hexamer primers to generate adequate amount of template. Because MDA favors a circular DNA template for maximum efficiency, its performance after RCA results in 3-5 μg of product in a short period, about 3 hours. Such an amount is sufficient for standard or PCR-free NGS library preparation. After heat-inactivation at 65° C. for 15 minutes, 20 U of T7 endonuclease I (NEB) was added for de-branching at 30° C. for 40 minutes. The final product was purified using QIAprep Spin Miniprep Kit (Qiagen). DNA quantitation, library preparation (1×250 nt single-end read), Illumina sequencing (NextSeq 500), and data analysis were performed as previously described (Wang et al., 2014; Ren et al., 2016; Wang et al., 2017; Gorse et al., 2017).

In order to assess the efficiency of TEEDseq, the output of four different reactions were compared. For three of the reactions, a serum sample from a blood donor was spiked with a 1,311-bp HBV fragment at $1 \times 10^6$ copies/mL. That sample was subjected to either direct sequencing using an Illumina Nextera Flex for plasma/serum kit (Option 1), the full TEEDseq protocol (Option 2), and a modified TEEDseq protocol using only Exonuclease I and Exonuclease III during the enzyme digestion step (Option 3). As a control, a serum sample that did not have any HBV fragment spiked in was also subjected to the full TEEDseq protocol (Option 4).

Figures 5A, 5B:
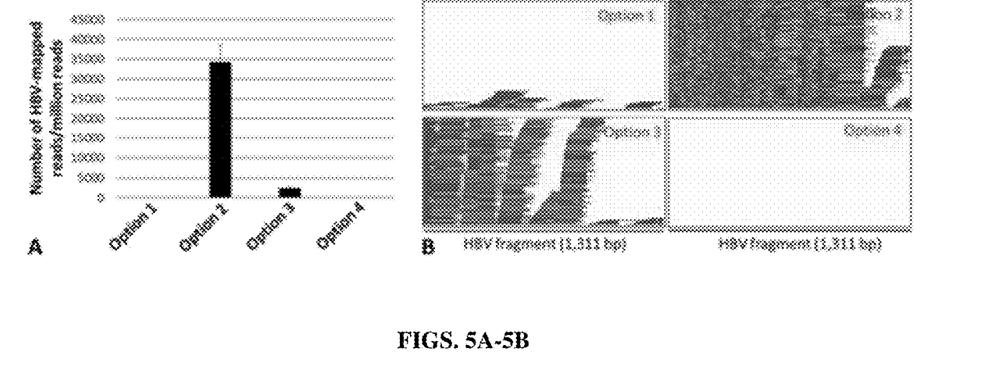

For each output, the HBV-mapped reads were normalized as the number of reads per million of total reads. After the normalization, the number of HBV-mapped reads detected were 65.1±16.5, 34299.3±4180.1, 2361.3±332.3, and zero for the Option 1, 2, 3, and 4, respectively (FIG. 5A). Compared to direct sequencing (Option 1), TEEDseq reached an enrichment of 526×. The full protocol of TEEDseq (Option 2), which including all five enzymes for digestion, was significantly more efficient than the omission of three restriction enzymes (AluI, HaeIII, and HpyCH4V) (Option 3), illustrating the role of dc⁷GTP in TEEDseq.

In the NGS data, the on-target reads (HBV-mapped reads) accounted for 3.42%. Off-target effects may come from non-specific priming at the step of primer extension since there is potential micro-homology between HBV and human genomes. More rigid primer design and conditions for primer extension may give a further enhancement for target-enrichment. However, a 3.42% on-target rate is already significantly improved since the on-target rates in HBV capture sequencing using probe-based strategies are well below 1% (Yan et al., 2015; Zhao et al., 2016). Indeed, a 1% on-target rate is a holy grail in NGS that demands target enrichment (Carpenter et al., 2013). Taken together, these experiments, using a small HBV fragment (1,311 bp) spiked in a serum sample, provide proof of concept evidence that TEEDseq is a simple and efficient method for target enrichment in NGS.

Example 3

In current clinical viral genome sequencing, next-generation sequencing (NGS) is a frequent choice that provides an unbiased high resolution of mutation profile in a genome-wide manner (Houldcroft et al., 2017). Because of an overwhelming dominance of human genetic content in clinical specimens, a major limitation of this approach is its low efficiency, which is rarely higher than 1% of viral sequencing reads in NGS output (Houldcroft et al., 2017). Among numerous virus-enriched methods, capture sequencing, employing a hybridization step after NGS library construction, comes out as the most efficient strategy to enrich viral sequences (Houldcroft et al., 2017). However, this strategy is associated with a dramatic cost increase as it requires the synthesis of expensive biotin labeled virus-specific probes (baits) and streptavidin beads (Briese et al., 2015). The inclusion of such a hybridization step after initial library preparation also makes the entire NGS pipeline a lengthy procedure. Most human viruses, such as hepatitis B virus (HBV), hepatitis C virus (HCV), HIV, and coronavirus, have a genome less than 30 kb in size.

If the viral on-target rate consistently exceeds 1%, current NGS approach is actually powerful enough to satisfy clinical and research needs. For instance, a 1% HCV on-target rate in 5 million of 2×150 bp paired ended reads give a depth at 1562×, which already crosses a saturation point (1100×) for HCV viral population dissection with a mutation frequency resolved at 1% (Wang et al., 2014). To achieve this goal, we provide an alternative option for viral sequence enrichment that does not require a probe-based hybridization step. Our method, named NGS with target enrichment via enzymatic digestion (TEEDseq), is dependent on 7-deaza-2'-deoxy-yguanosine 5'-triphosphate (c7dGTP), an analog of deoxyguanosine triphosphate (dGTP). Due to its ability to relax DNA secondary structure, c$^7$dGTP is widely used in PCR and Sanger sequencing (McConlogue et al., 1998; Motz et al., 2000). DNA molecules composed of c$^7$dGTP show steric alteration that is resistant to some restriction enzymes with the recognition motifs containing guanosine (Grime et al., 1991). This unique characteristic of c$^7$dGTP was used to accomplish the enrichment of a sequencing target.

Another workflow of TEEDseq was evaluated using a healthy donor serum sample spiked with a 1311-bp HBV PCR fragment at a concentration of 1×10$^6$ copies/mL, mimicking a concentration from viruses like HCV and HBV (Table 1) (Easterbrook et al., 2017). Total DNA was extracted from 0.5 mL of serum by QIAamp MinElute ccfDNA Kit (Qiagen, Valencia, Calif.) and eluted into 20 µL Tris buffer. Entire 20 µL extracted DNA was used for 5-cycle primer extension under 1 unit of Q5 DNA polymerase, 0.4 µM primer HBVR4 (Table 1), and 0.8 mM of dNTPs in which dGTP was completely replaced by c$^7$dGTP. The reaction was purified using MinElute PCR Purification Kit (Qiagen) and eluted into 20 µL Tris buffer, followed by ligation in 30 µL reaction consisting of 10 U T4 DNA ligase and 0.5 µM of the splinter at 14° C. overnight. After heat inactivation, the enzyme complex (AluI 10 U, HeaIII 10 U, HpyCH4V 5 U, Exonuclease I 50 U, and Exonuclease III 20 U) was added buffer. 3 h after the incubation at 37° C., the reaction was heat-inactivated and used for RCA with 1 µM target-specific primer HBVR5 (Table 1) at 30° C. for the first 12 h and then 4 h at 28° C. with 80 µM of C28 primer (Table 1). The final product was around 12 kb in size with an average yield of 1.8 µg after purification using QIAprep Spin Miniprep Kit (Qiagen). The product was subjected to Illumina sequencing (1×250 nt single-end read), followed by data analysis as we previously described (Wang et al., 2017; Gorse et al., 2017). We tested four options: full TEEDseq protocol (a), TEEDseq with the omission of three restriction enzyme (b), direct sequencing using Illumina Nextera Flex for plasma/serum kit (c), and full TEEDseq using the same serum sample without the spike-in of the HBV fragment (d). Each option was set for three technical replicates.

Figure 5C:
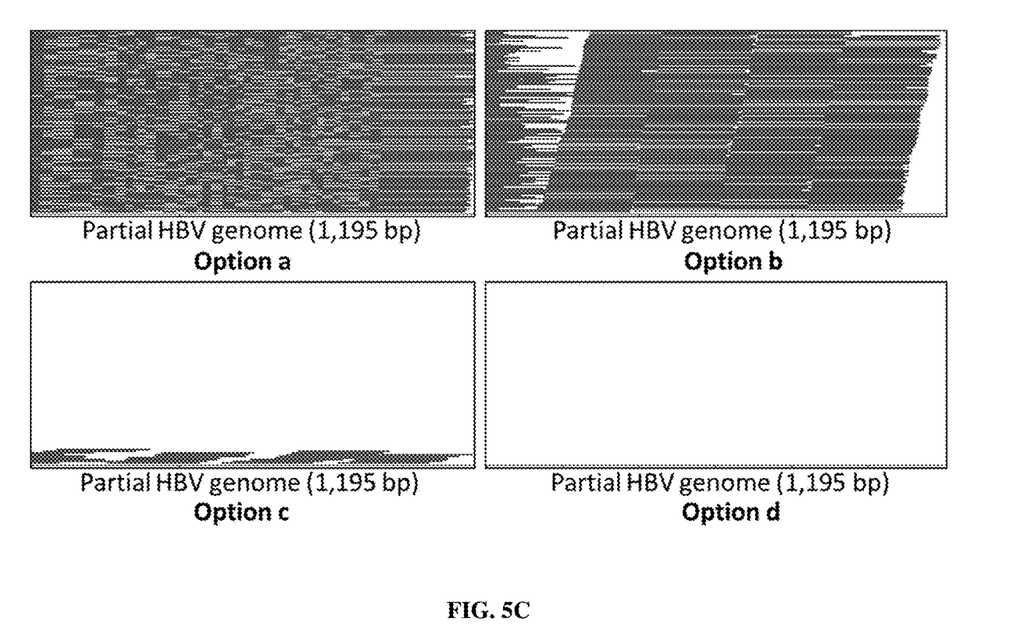
(FIG. 5C) Read-alignment on 1195-bp HBV genome sequence from the HBVR4 priming site was viewed in bam file using BamView (Carver et al., 2013). Reads with matching start and end positions were collapsed into one line and are shown in green. Option a, b, and c used a serum sample spiked with 1311-bp HBV fragment. Option d had no HBV fragment spiked in the serum and served as a control. Each option was shown with the numbers (average and standard derivation) of HBV-mapped and total reads from three technical replicates after the quality control.

After read quality control (Wang et al., 2017; Gorse et al., 2017), one million of total reads had HBV-mapped reads at 33,153±3900 (3.31±0.39%), 2638±750 (0.26±0.07%), 73±21 (0.007±0.0002%), and zero for options a, b, c, and d, respectively (FIG. 5C). TEEDseq reached an enrichment 454× that of direct sequencing (option c). The recovery of HBV-mapped reads was 12.6 times higher in option a than in option b, illustrating the pivotal role of the three restriction enzymes. Using HiCUP (Wingett et al., 2015), these enzymes together have 36,535,384 cuts (AluI 13,085,321; HaeIII 8,582,925; HpyCH4V 14,867,138) on the human genome (building GRCh38). Their combination with exonucleases efficiently digested non-target background sequences.

Our method consists of four steps: primer extension, splinter ligation, enzymatic digestion, and rolling circle amplification (RCA) (FIG. 2). Using a serum sample spiked with a partial HBV genome (1311 bp), TEEDseq achieved a 3.31% mapping rate. Under a probe-based hybridization strategy, genome-wide HBV capture sequencing does not necessarily have a high on-target rate, for instance, <1% in a recent report (Zhao et al., 2016). Off-target effect may come from non-specific priming since there is significant microhomology between HBV and the human genome (Lin, 2016). A more rigid primer design and conditions for primer extension could further enhance the enrichment.

In addition, TEEDseq has several technical features worthy of attention. Serum DNA is regarded as a low-biomass sample. Its low DNA concentration, 435 ng/mL in the current study, naturally favors intracellular ligation that can be further facilitated using a splinter. Because intermolecular ligation is suppressed at a low DNA concentration, high concentration of templates, such as DNA extracted from tissue samples, need to be diluted prior to the ligation (Mason et al., 2016). Second, we applied two-phase RCA amplification, target-specific and non-specific. The short incubation of non-specific RCA suppresses the amplification of contaminated sequences in the reagents, as observed in our recent studies (Li et al., 2019; Ren et al., 2020). Third, TEEDseq requires purification after primer extension. Afterwards, ligation, digestion, and RCA do not need purification because all enzymes have optimal activity in the Cut-Smart buffer (NEB). Therefore, these reactions can be conducted successively in the same tube. Finally, phi29 DNA polymerase used in RCA has a strong stand-displacement activity. This activity results in a hyperbranched structure of the final product that usually has a large size more than 10 kb (Binga et al., 2008). Therefore, the final product can be directly used for fragmentation in NGS library preparation without the need of additional procedure, such as concatemerization. Taken together, our experiment, using a partial HBV genome (1311 bp) spiked in a serum sample, provides concept evidence that TEEDseq is a simple and cost-effective method for target enrichment in NGS. By using multiple primers to cover target genomes in primer extension, it can be applied to clinical viral sequencing as well as human genomic research.

TABLE 1

List of oligonucleotides

| Oligonucleotide | Polarity | Sequence (5'→3') | Position | Product size/note |
|---|---|---|---|---|
| HBVF1 | Sense | actctctcgtccccttctcc (SEQ ID NO: 2) | 1479-1498 | 504 bp |
| HBVR1 | Antisense | tgacggaaggaaagaagtcag (SEQ ID NO: 3) | 1962-1982 | |
| HBVR1$^P$ | Antisense | $^P$tgacggaaggaaagaagtcag (SEQ ID NO: 3) | 1962-1986 | |
| HBVF2 | Sense | ccttctccgtctgccgttc (SEQ ID NO: 4) | 1491-1509 | 488 bp |

TABLE 1-continued

List of oligonucleotides

| Oligonucleotide | Polarity | Sequence (5'→3') | Position | Product size/note |
|---|---|---|---|---|
| HBVR2 | Antisense | ggaaggaaagaagtcagaaggc (SEQ ID NO: 5) | 1957-1978 | |
| HBVF3 | Sense | aacaggctttcactttctcgc (SEQ ID NO: 7) | 1082-1102 | 1311 bp |
| HBVR3 | Antisense | cgagggagttcttcttctaggg (SEQ ID NO: 8) | 2371-2392 | |
| HBVR4 | Antisense | $^P$tccacactccgaaagagacc (SEQ ID NO: 11) | 2257-2276 | |
| Splinter | NA | nnnnnnaggtgtgtSp3 (SEQ ID NO: 12) | To facilitate intramolecular ligation | |
| HBVR5 | Antisense | tgtgtg*g*a (SEQ ID NO: 13) | Target-specific RCA | |
| C28 | NA | Sp18nnn*n*n (SEQ ID NO: 14) | Non-specific RCA | |

Position is according to the full-length HBV genome under GenBank accession number AB241115. Star donated phosphorothioate bonds to resist exonuclease activity of phi29 DNA polymerase. P in superscript indicated the modification of phosphate at the 5' ends. C28 is the primer to eliminate primer-mediated artifacts from phi29 DNA polymerase-based multiple displacement amplification in our previous study (Wang et al., 2017). Sp3, C3 spacer to block self-ligation of the splinter; Sp18, C18 spacer; NA, not applicable. All oligonucleotides were ordered from the Integrated DNA Technologies, Coralville, IA.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Binga E K, Lasken R S, Neufeld J D. Something from (almost) nothing: the impact of multiple displacement amplification on microbial ecology. ISME J. 2008; 2:233-41.

Briese T, Kapoor A, Mishra N, Jain K, Kumar A, Jabado O J, et al. Virome capture sequencing enables sensitive viral diagnosis and comprehensive virome analysis. MBio. 2015; 6:e01491.

Broadbent S, van der Woude M, Aziz N. Accurate and simple sizing of primer extension products using a non-radioactive approach facilitates identification of transcription initiation sites. J Microbiol Methods 2010; 81:256-8.

Carpenter M L, Buenrostro J D, Valdiosera C, Schroeder H, Allentoft M E, Sikora M, et al. Pulling out the 1%: whole-genome capture for the targeted enrichment of ancient DNA sequencing libraries. Am J Hum Genet. 2013; 93:852-64.

Carver T, Harris S R, Otto T D, Berriman M, Parkhill J, McQuillan J A. BamView: visualizing and interpretation of next-generation sequencing read alignments. Brief Bioinform. 2013; 14:203-12.

Civit L, Fragoso A, O'Sullivan C K. Evaluation of techniques for generation of single-stranded DNA for quantitative detection. Anal Biochem. 2012; 431:132-8.

Dahl F, Baner J, Gullberg M, Mendel-Hartvig M, Landegren U, Nilsson M. Circle-to-circle amplification for precise and sensitive DNA analysis. Proc Natl Acad Sci USA. 2004; 101:4548-53.

Easterbrook P J, Roberts T, Sands A, Peeling R. Diagnosis of viral hepatitis. Curr Opin HIV AIDS. 2017; 12:302-14.

Gansauge M T, Gerber T, Glocke I, Korlevic P, Lippik L, Nagel S, Riehl L M, Schmidt A, Meyer M. Single-stranded DNA library preparation from highly degraded DNA using T4 DNA ligase. Nucleic Acids Res. 2017; 45:e79.

Gorse G J, Gira B. Patela G B and Fan X. Interpatient Mutation Spectrum of Human Coronavirus-OC43 Revealed by Illumina Sequencing. J Med Virol 2017; 89:1330-1338.

Grime S K, Martin R L, Holaway B L. Inhibition of restriction enzyme cleavage of DNA modified with 7-deaza-dGTP. Nucleic Acids Res. 1991; 19:2791.

Hayer J, Jadeau F, Deleage G, Kay A, Zoulim F, Combet C. HBVdb: a knowledge database for Hepatitis B Virus. Nucleic Acids Res. 2013; 41 (Database issue):D566-70.

Head S R, Komori H K, LaMere S A, Whisenant T, Van Nieuwerburgh F, Salomon D R, Ordoukhanian P. Library construction for next-generation sequencing: overviews and challenges. Biotechniques 2014; 56:61-77.

Houldcroft C J, Beale M A, Breuer J. Clinical and biological insights from viral genome sequencing. Nat Rev Microbiol. 2017; 15:183-92.

Illumina: Target enrichment; available on the world wide web at illumina.com/techniques/sequencing/dna-sequencing/targeted-resequencing/target-enrichment.html Kuiken C, Yusim K, Boykin L, Richardson R. The Los Alamos HCV Sequence Database. B ioinformatics 2005; 21:379-84.

Kwok C K, Ding Y, Sherlock M E, Assmann S M, Bevilacqua P C. A hybridization-based approach for quantitative and low-bias single-stranded DNA ligation. Anal Biochem. 2013; 435:181-6.

Li G, Zhou Z, Yao L, Xu Y, Wang L, Fan X. Full annotation of serum virome in Chinese blood donors with elevated alanine aminotransferase levels. Transfusion. 2019; 59:3177-85.

Lin S. Analysis of the complexity of HBV-host junction sequences in patients with HBV-related hepatocellular carcinoma. Philadelphia: Ph.D. thesis. Drexel University College of Medicine; 2016.

Mason W S, Gill U S, Litwin S, Zhou Y, Peri S, Pop O, et al. HBV DNA integration and clonal hepatocyte expansion in chronic hepatitis B patients considered immune tolerant. Gastroenterology. 2016; 151:986-98.

McConlogue L, Brow M A, Innis M A. Structure-independent DNA amplification by PCR using 7-deaza-2'-deoxyguanosine. Nucleic Acids Res. 1988; 16:9869.

McDonald B R, Contente-Cuomo T, Sammut S J, Odenheimer-Bergman A, Ernst B, Perdigones N, et al. Personalized circulating tumor DNA analysis to detect residual disease after neoadjuvant therapy in breast cancer. Sci Transl Med. 2019; 11(504). pii: eaax7392.

Motz M, Pääbo S, Kilger C. Improved cycle sequencing of G C-rich templates by a combination of nucleotide analogs. Biotechniques. 2000; 29:268-70.

Ren Y, Wang W, Zhang X, Xu Y, Di Bisceglie A M, Fan X. Evidence for deleterious hepatitis C virus quasispecies mutation loads that differentiate the response patterns in IFN-based antiviral therapy. J Gen Virol. 2016; 97:334-43.

Ren Y, Xu Y, Lee W M, Di Bisceglie A M, Fan X. In-depth serum virome analysis in acute liver failure patients with indeterminate etiology. Arch Virol. 2020; 165:127-35.

Valenzuela P, Rall L, Zaldivar M, Quiroga M, Gray P, Rutter W. The nucleotide sequence of the hepatitis B viral genome and the identification of the major viral genes. ICN-UCLA Symp Mol Cell Biol. 1980; 18:57-70.

Wang W, Zhang X, Xu Y, Weinstock G M, Di Bisceglie A M and Fan X. High-resolution quantification of hepatitis C virus genome-wide mutation load and its correlation with the outcome of peginterferon-alpha2a and ribavirin combination therapy. PLoS One 2014; 9:e10013110

Wang W, Ren Y, Xu Y, Crosby S, Di Bisceglie A M, Fan X. Template-dependent multiple displacement amplification applied to profile human circulating RNA. BioTechniques 2017; 63:21-27.

Weiss J, Zucht H D, Forssmann W G. Amplification of gene fragments with very high G/C content: c7dGTP and the problem of visualizing the amplification products. PCR Methods Appl. 1994; 4:124-5.

Wingett S, Ewels P, Furlan-Magaril M, Nagano T, Schoenfelder S, Fraser P, Andrews S. HiCUP: pipeline for mapping and processing Hi-C data. F1000Res 2015; 4:1310.

Yan H, Yang Y, Zhang L, Tang G, Wang Y, Xue G, Zhou W, Sun S. Characterization of the genotype and integration patterns of hepatitis B virus in early- and late-onset hepatocellular carcinoma. Hepatology 2015; 61:1821-31.

Zhao L H, Liu X, Yan H X, Li W Y, Zeng X, Yang Y, et al. Genomic and oncogenic preference of HBV integration in hepatocellular carcinoma. Nat Commun. 2016; 7:12992.

---

What is claimed is:

1. A method of preparing a target enriched nucleic acid template for next-generation sequencing, the method comprising:
   (a) incubating a population of nucleic acid molecules comprising the template nucleic acid with a primer that hybridizes to the template nucleic acid, $c^7dGTP$, dCTP, dATP, dTTP, and a DNA polymerase under conditions to allow for primer extension;
   (b) incubating the product of step (a) with a splinter oligonucleotide and T4 DNA ligase under conditions to allow for the self-ligation of the extension product of step (a);
   (c) incubating the product of step (b) with $c^7dGTP$-resistant restriction enzymes, Exonuclease I, and Exonuclease III under conditions to allow for the digestion of non-target and background nucleic acid;
   (d) incubating the product of step (c) with a primer that hybridizes to the primer used in step (a), dNTPs, and a DNA polymerase under conditions to allow for rolling circle amplification; and
   (e) incubating the product of step (d) with degenerate primers, dNTPs, and a DNA polymerase under conditions to allow for rolling circle amplification, thereby generating a target enriched nucleic acid template for next-generation sequencing.

2. The method of claim 1, wherein the template nucleic acid is DNA.

3. The method of claim 2, wherein the DNA polymerase used in step (a) is a DNA-dependent DNA polymerase.

4. The method of claim 1, wherein the template nucleic acid is RNA.

5. The method of claim 4, wherein the DNA polymerase used in step (a) is an RNA-dependent DNA polymerase.

6. The method of claim 1, wherein the $c^7dGTP$-resistant restriction enzymes are AluI, HaeIII, and/or HpyCH4V.

7. The method of claim 1, wherein the primer comprises a phosphate on the 5' end.

8. The method of claim 1, wherein the 3' end of the primer has a sequence that hybridizes to the template nucleic acid, a degenerate sequence, or a poly-T sequence.

9. The method of claim 1, wherein step (a) comprises 5-10 cycles of primer extension.

10. The method of claim 1, wherein the splinter oligonucleotide hybridizes to a rare restriction site at the 5' end of the primer used in step (a).

11. The method of claim 1, wherein the splinter oligonucleotide has a C3 spacer at its 3' end.

12. The method of claim 1, wherein the splinter oligonucleotide has a degenerate sequence at its 5' end.

13. The method of claim 1, wherein the product of step (a) is purified prior to performing step (b).

14. The method of claim 1, wherein the DNA polymerase used in step (d) is phi29 DNA polymerase.

15. The method of claim 1, wherein the primer used in step (d) comprises phosphorothioate bonds.

16. The method of claim 1, wherein the reaction of step (c) is heat inactivated prior to performing step (d).

17. The method of claim 1, wherein steps (b) through (e) are performed in the same tube, without exchanging the buffer, without removing any components from the previous reactions, and/or without any intervening purification steps.

18. The method of claim 1, wherein the template nucleic acid is (a) a rare species within the population of nucleic acid molecules, (b) a viral or bacterial species and the population of nucleic acid molecules comprises nucleic acid molecules extracted from a patient sample, (c) a poorly expressed RNA and the population of nucleic acid molecules comprises nucleic acid molecules extracted from a patient sample, and/or (d) a fusion gene and the population of nucleic acid molecules comprises nucleic acid molecules extracted from a patient sample.

* * * * *